(12) United States Patent
Van Zutphen et al.

(10) Patent No.: US 11,927,583 B2
(45) Date of Patent: Mar. 12, 2024

(54) MEASURING DEVICE AND METHOD FOR A CONTACTLESS ANALYSIS OF A FOOD PRODUCT IN A PRODUCTION LINE

(71) Applicant: KAAK GROEP B.V., Terborg (NL)

(72) Inventors: Pieter Petrus Hendrikus Van Zutphen, Terborg (NL); Sjoerd Gerardus Johannes Raben, Terborg (NL); Franciscus Quirinus Fredrik Verouden, Terborg (NL); Lodewijk Stephanus Margaretha Joseph Van Der Borg, Terborg (NL); Maria Kokkoti, Terborg (NL)

(73) Assignee: KAAK GROEP B.V., Terborg (NL)

( * ) Notice: Subject to any disclaimer, the term of this patent is extended or adjusted under 35 U.S.C. 154(b) by 471 days.

(21) Appl. No.: 17/276,268

(22) PCT Filed: Sep. 16, 2019

(86) PCT No.: PCT/NL2019/050601
§ 371 (c)(1),
(2) Date: Mar. 15, 2021

(87) PCT Pub. No.: WO2020/055258
PCT Pub. Date: Mar. 19, 2020

(65) Prior Publication Data
US 2022/0026408 A1  Jan. 27, 2022

(30) Foreign Application Priority Data

Sep. 14, 2018 (NL) .................................... 2021642

(51) Int. Cl.
*G01J 5/00* (2022.01)
*A21C 13/02* (2006.01)
(Continued)

(52) U.S. Cl.
CPC .............. *G01N 33/10* (2013.01); *A21C 13/02* (2013.01); *G01J 5/00* (2013.01); *G01N 11/00* (2013.01); *G01S 15/08* (2013.01); *G01S 17/08* (2013.01)

(58) Field of Classification Search
CPC . G01N 33/10; G01N 11/00; G01J 5/00; G01S 15/08; G01S 17/08
See application file for complete search history.

(56) References Cited

U.S. PATENT DOCUMENTS 2,147,024 A    2/1939 Frisk
5,372,030 A *  12/1994 Prussia .................... G01N 3/40
                                                356/3
(Continued)

FOREIGN PATENT DOCUMENTS

AT         393914 B      1/1992
CN      108956376 A  * 12/2018 ............. G01N 11/00
(Continued)

OTHER PUBLICATIONS

International Search Report and Written Opinion from PCT Application No. PCT/NL2019/050601, dated Dec. 13, 2019.
(Continued)

*Primary Examiner* — Jamel E Williams
(74) *Attorney, Agent, or Firm* — Workman Nydegger

(57) ABSTRACT

The invention relates to a device and a method for a contactless analysis of a product, in particular for the contactless analysis of a dough product. The device comprises a distance sensor configured for measuring a distance between the device and the product, and a nozzle configured for directing a jet of pressurized fluid to a position on a surface of said product. The distance sensor is arranged for measuring the distance between the device and the position of the surface where the jet of pressurized fluid is directed to. Preferably, the distance sensor is at least partially
(Continued)

arranged in the nozzle, preferably substantially in the center of said nozzle.

22 Claims, 13 Drawing Sheets

(51) Int. Cl.
*G01N 11/00* (2006.01)
*G01N 33/10* (2006.01)
*G01S 15/08* (2006.01)
*G01S 17/08* (2006.01)

(56) References Cited

U.S. PATENT DOCUMENTS

| | | | |
|---|---|---|---|
| 6,397,734 B1 | 6/2002 | Atzinger | |
| 2007/0000442 A1* | 1/2007 | Schucker | ............... B25J 19/023 |
| | | | 118/713 |

FOREIGN PATENT DOCUMENTS

| | | | | |
|---|---|---|---|---|
| CN | 108956377 A | * | 12/2018 | ............. G01N 11/00 |
| DE | 9001451 U1 | | 6/1991 | |
| EP | 0214100 A1 | | 3/1987 | |
| EP | 1096857 A1 | | 5/2001 | |
| WO | WO-2020055258 A1 | * | 3/2020 | ............. A21C 13/00 |

OTHER PUBLICATIONS

Search Report from corresponding NL Application No. NL2021642, dated May 13, 2019.

* cited by examiner

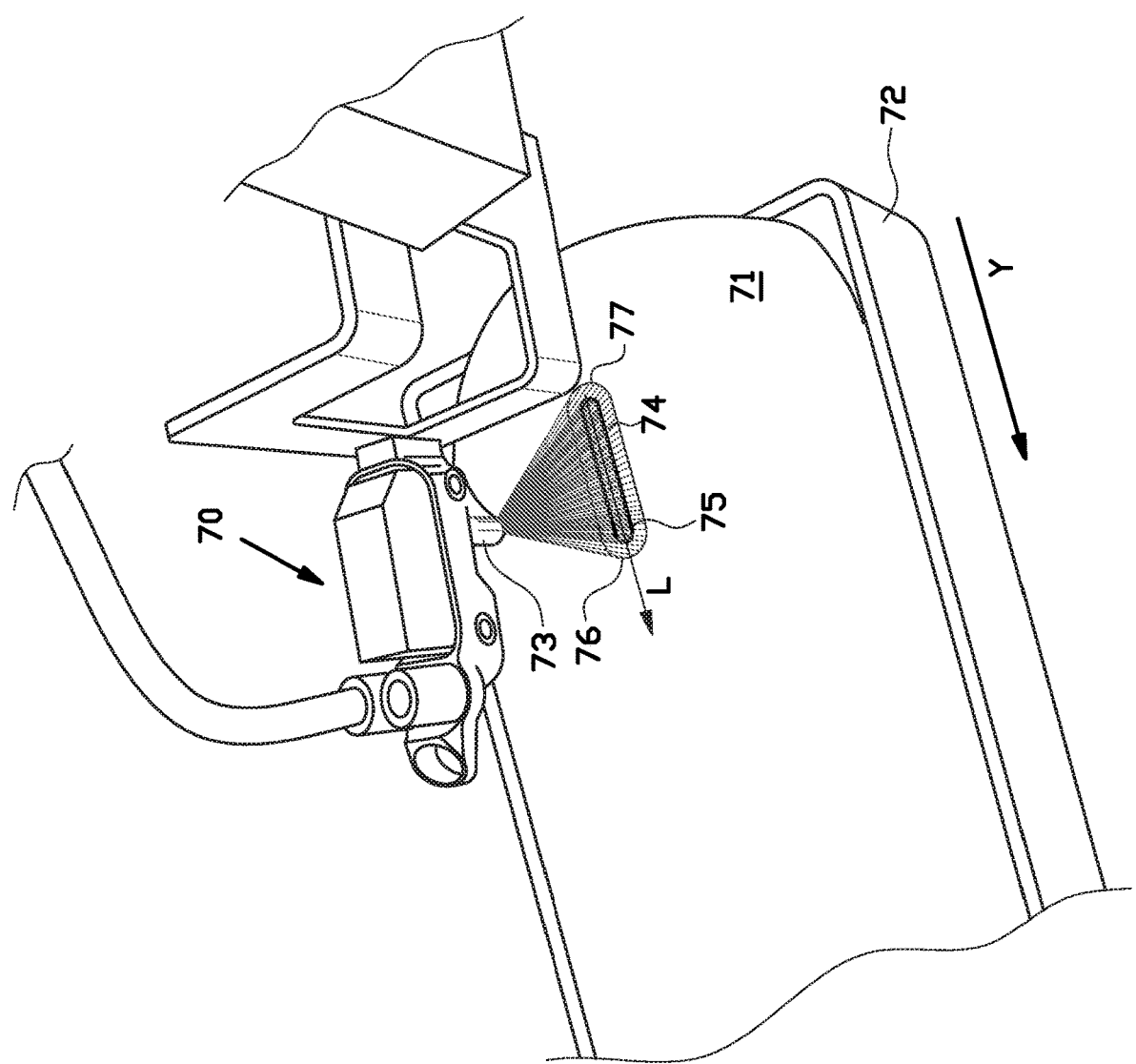

MEASURING DEVICE AND METHOD FOR A CONTACTLESS ANALYSIS OF A FOOD PRODUCT IN A PRODUCTION LINE

BACKGROUND

Field of the Invention

The invention relates to a measuring device which is configured for a contactless analysis of a food product in a production line, in particular for contactless medium analysis of food products, and more in particular for dough products. In addition, the invention relates to a method for a contactless analysis of a product in a production line.

Description of the Related Art

U.S. Pat. No. 2,147,024 describes a device for detecting the proofing condition of dough lumps, which are subjected to a proofing process in a proofing chamber. During the proofing process, the dough lumps experience an increase in volume. The device comprises an electrical switch which is provided on a framework which allows to adjust the position of the switch relative to a support surface for the dough lumps in the proofing chamber. The electrical switch is provided with a convex contact element which is adapted for engagement by dough raising there-below. When the dough has raised sufficiently to engage the contact element and deflect the electrical switch, the electrical switch actuates an alarm device signaling that the dough has raised to a desired height.

A further development of such a measuring device is disclosed in EP 1 096 857 B1, which describes a device comprising a distance sensor, associated with at least one of the dough lumps provided in the proofing chamber, which, at least when the thickness of the dough lump achieves a pre-determined intended value, which is correlated with a desired degree of ripeness of the dough lump, produces a therefore characteristic output signal. The distance sensor is designed and/or arranged such that it detects the height of the dough lump above a support surface. The distance sensor is an ultra-sonic sensor which operates on the principle of the travel time lapse of ultra-sonic signals. The distance sensor is provided on a framework employable in the proofing chamber, which can be placed on the proofing sheet in the chamber.

SUMMARY OF THE INVENTION

A disadvantage of the known device(s) is that they provide very limited information, in particular only information is obtained about the increase in volume of the dough lumps.

It is an object of the present invention to provide a device and a method which allows a more detailed analysis of the products, in particular which allows to obtain material properties of the products.

According to a first aspect, the invention provides a device for performing an analysis of a food product, in particular a dough product, wherein said device comprising:
a distance sensor configured for contactless measuring a distance between the device and a surface of the food product, and
a nozzle configured for directing a jet of pressurized fluid to a position on the surface of said food product, preferably wherein the jet of pressurized fluid is configured for providing a deformation of the surface of said food product, wherein the distance sensor is arranged for measuring the distance between the device and the position on the surface of the food product where the jet of pressurized fluid is and/or has been directed to, preferably for monitoring a development and/or a decrease or removal of the deformation of the surface of said food product.

Accordingly, the device according to the present invention allows to apply a force to the position on the surface of a product by directing a jet of pressurized fluid to said position on the surface. In addition, the device comprises a distance sensor for measuring the distance between the device and the position of the surface, in particular at the position of the surface where the jet of pressurized fluid is directed to. Any deformation of the surface at said position where the jet of pressurized fluid is directed to can be measured by the distance sensor. In addition or alternatively, the decrease or removal of the deformation of the surface at said position where the jet of pressurized fluid had been directed to can be measured by the distance sensor.

Such a sensor is particularly advantageous for analyzing deformable products, such as dough products. A dough is a visco-elastic material, which can be characterized by material parameters such as, inter alia, a viscosity and elasticity. This viscosity and elasticity is different for different types of dough and changes also during the production process due to the various treatments of the dough before the dough product is finally backed in an oven. In particular the structure of the dough may change during the mixing, kneading and proofing of the dough.

Because of the viscosity and elasticity of dough, the surface of the dough will develop a local deformation when a force is applied to said surface of the dough, and this deformation will at least partially disappear when the force is removed from said surface of the dough. This development and/or removal of the deformation can be monitored by means of the distance sensor. In particular from said development and/or removal of the deformation of the surface by the jet or pressurized fluid, a measure of material properties such as viscosity and elasticity, can be determined, for example by analyzing the data with a mathematical deformation model.

In particular when analyzing food products, such as dough products, a device for contactless analysis is advantageous, in particular to substantially prevent contamination of and/or damage to the products. In addition, the device is spaced apart from the product and is not in contact with the product, and therefor also contamination of the device is at least substantially prevented. When using the device of the present invention, only the jet of pressurized fluid comes in contact with the product. Accordingly, it is preferred to use clean pressurized fluid and/or the filter the pressurized fluid before it is directed to the product.

In an embodiment, the distance sensor is configured for measuring the distance between the device and substantially a center of the position of the surface where the jet of pressurized fluid is directed to. This allows to measure the deformation of the surface of the product substantially in the center of the position where the jet of pressurized fluid applies a force to the surface of the product. In particular when analyzing dough products, the deformation of the surface of said dough product is substantially only at the position of the surface where the jet of pressurized fluid impinges on the dough product.

In an embodiment, the distance sensor is at least partially arranged in the nozzle, preferably substantially in the center of said nozzle. In use, the distance sensor is at least partially arranged in the center of the jet of pressurized fluid coming out of the nozzle. By arranging the distance sensor at least partially in the nozzle, the distance sensor can measure the distance between the device and the position where the jet of pressurized fluid impinges on the surface of the product, substantially independent from the distance between the product and the device.

In an embodiment, the distance sensor comprises an illuminating beam source for projecting a light beam to the position on the surface of the product, and a light collecting unit for receiving light reflected from said surface of the product, wherein the light collecting unit is configured for providing a measure of the distance between the light collecting unit and the position on the surface of the product where the light beam impinges on said surface. Accordingly, the device according to this embodiment comprises an optical distance sensor.

In an embodiment, the illuminating beam source is configured for projecting the light beam along a central axis of the jet of pressurized fluid from the nozzle. In an embodiment, the illuminating beam source comprises a light delivering member which is arranged in the nozzle. The light delivering member may comprise a light source, such as a lamp, LED or Laser, or may comprise a optical fiber. Accordingly, the light beam travels along the central axis of the jet of pressurized fluid, and as a result the light beam is arranged substantially in the center of the position where the jet of pressurized fluid impinges on the surface of the product, independent from the distance between the product and the device.

In an embodiment, the light collecting unit comprises one or more lenses for projecting and/or imaging the light reflected from said surface of the product on a light sensor, preferably wherein the light sensor comprises a CCD sensor array. By analyzing an image or part of an image of the light beam impinging on the surface, the distance between the device and the surface of the product can be established.

For example, when using a slightly diverging of focused light beam, the diameter of the light spot on the surface of the product will increase or decrease as a function of the distance between the device and the surface of the product.

Preferably, the one or more lenses are configured such that an optical axis of the one or more lenses is arranged at a sharp angle to the light beam. In particular the optical axis is arranged to intersect the light beam at a distance from the device, preferably at or near a distance from the device where the surface of the product is expected. Accordingly, the position of the light spot in the image on the light sensor will move as a function of the distance between the device and the surface of the product.

In an embodiment, the device comprises a supply tube for supplying said fluid, wherein said supply tube comprises a first branch for providing at least part of said fluid in the supply tube to the light collecting unit.

Alternatively, in an embodiment, the device comprises a first supply tube for supplying said fluid, and a second supply tube for supplying a cleaning fluid to the light collecting unit. The cleaning fluid may be the same as the fluid used for the jet of pressurized fluid, or may be a different fluid.

The later two embodiments are in particular advantageous in a dusty environment, because dust from said environment may accumulate on the optics of the sensor, such as the one or more lenses. By providing at least part of the fluid or a cleaning fluid to the light collecting unit, the part of the fluid or cleaning fluid can be used for blowing dust away from the optics, and to clean the optics of the sensor.

In an embodiment, the distance sensor comprises an ultrasonic sensor comprising a transceiver or a combination of a transmitter and a receiver. Because ultrasonic sensors use sound rather than light for detection, they work in applications where light sensors may not. Ultrasonic sensors are advantageous for translucent products. Target color or reflectivity substantially does not affect ultrasonic sensors, which can also operate reliably in high-glare environments. In addition, ultrasonic sensors are not or to a lesser extend affected by dusty environments, for example as in a bread production line.

In an embodiment, at least the transmitter or the transceiver is at least partially arranged in the nozzle. In an embodiment, at least the transmitter or the transceiver is at least partially arranged substantially in the center of the nozzle. Accordingly, the sound or sound pulse from the transmitter or the transceiver travels substantially along the central axis of the jet of pressurized fluid, and as a result the sound or sound pulse is arranged for measuring the distance substantially in the center of the position where the jet of pressurized fluid impinges on the surface of the product, independent from the distance between the product and the device.

In an embodiment, the nozzle comprises one or more jet vectoring members, preferably wherein the one or more jet vectoring members are arranged inside said nozzle. In an embodiment, the one or more jet vectoring members preferably comprises a series of separation walls which extend in a direction substantially parallel to a central axis of the jet or wherein the one or more jet vectoring members comprises a series of substantially parallel tubes which extend in a direction substantially parallel to a central axis of the jet. The vectoring members are arranged to provide a substantially parallel jet of pressurized air, at least in or near the measuring range. Such a substantially parallel jet of pressurized air, applies the same magnitude of force to the surface of the product, substantially independent of the distance between the device and the surface of the product, at least in said measuring range.

In an embodiment, the device comprises a temperature sensor, wherein the temperature sensor is configured for measuring a temperature of said product. In an embodiment, the temperature sensor comprises a contactless temperature sensor. In an embodiment the temperature sensor comprises an infra-red temperature sensor. Usually material properties of the products, such as viscosity and elasticity, are temperature dependent. By also measuring the temperature of at least the surface of the product, the temperature of the product can be taken in consideration when determining the material properties.

In an embodiment, the device comprises a supply tube for supplying said fluid, wherein said supply tube comprises a second branch for providing at least part of said fluid in the supply tube to the temperature sensor.

Alternatively, in an embodiment, the device comprises a first supply tube for supplying said fluid, and a further supply tube for supplying a cleaning fluid to the temperature sensor.

Again, the later two embodiments are in particular advantageous in a dusty environment, because dust from said environment may accumulate on the temperature sensor. By providing at least part of the fluid or cleaning fluid to the temperature sensor, the part of the fluid or the cleaning fluid can be used for blowing dust away from the temperature sensor, and to clean the temperature sensor.

In an embodiment, the fluid comprises a gas, preferably wherein the fluid comprises nitrogen gas or air.

According to a second aspect, the invention provides an assembly for processing of products, in particular for processing of dough, wherein the assembly comprising:

a processing and/or conveying apparatus for said products, and a device for a contactless analysis of a product as described above, wherein the device is arranged for directing the jet of pressurized fluid to a position on a surface of one of said products in the assembly.

In an embodiment, the assembly comprises a conveying apparatus for conveying said at least one of said products in the assembly, and wherein the device is arranged for moving substantially synchronously with said at least one of said products in the assembly at least during an acquisition of measurements on the at least one of said product by the device. Accordingly the device for measuring and the product on which measurements are perform move substantially synchronously, and at least during the measurements the device is arranged at a substantially fixed position with respect to the product on which the measurements are performed.

In an alternative embodiment, the assembly comprises a conveying apparatus for conveying the products in a conveyance direction in the assembly, and wherein the device comprises a nozzle for producing a jet of pressurized fluid with an elongated cross-section, wherein a longitudinal direction of said elongated cross-section is arranged substantially parallel to the conveyance direction. Preferably, the distance sensor is arranged at or near an end of the elongated cross-section in the longitudinal direction, preferably at the upstream end with respect to the conveyance direction. Such a device allows to measure the development of the deformation of the surface of a product that moves with respect to the device. Accordingly the device can be arranged on a substantially stationary position at the assembly and does not have to travel along with the conveyed products.

In a further alternative embodiment, the assembly comprises a conveying apparatus for conveying the products in a conveyance direction in the assembly, and wherein the device comprises a series of nozzles each one for producing a jet of pressurized fluid, wherein said series of nozzles are arranged on a line which extends in a direction substantially parallel to the conveyance direction. Preferably, the distance sensor is arranged in or at the nozzle which is arranged at the upstream end of the series of nozzles. Such a device allows to measure the development of the deformation of the surface of a product produced by the jets of compressed fluid from successive nozzles, when the product moves with respect to the series of nozzles of the device. Accordingly the device can be arranged on a substantially stationary position at the assembly and does not have to travel along with the conveyed products.

In a further alternative embodiment, the assembly comprises a conveying apparatus for conveying the products in a conveyance direction in the assembly, and wherein the device comprises a line shaped illuminating beam, wherein said line shaped illuminating beam is configured for providing a line of light on the product surface, which line of light extends in a direction substantially parallel to the conveyance direction. Preferably, the distance sensor comprises a camera and an image analysis processor which is configured to analyze a deformation of said line of light due to the development and/or a removal of the deformation of the surface of said food product by the jet of compressed fluid. Such a device allows to measure the development of the deformation of the surface of a product produced by the jet of compressed fluid from successive positions along the line of light, when the product moves with respect to the line of light. Accordingly the device can be arranged on a substantially stationary position at the assembly and does not have to travel along with the conveyed products.

According to a third aspect, the invention provides a method for a contactless analysis of a product, preferably using a device for performing an analysis of a food product as described above, wherein said method comprising the steps of:

contactless measuring a distance between the device and a surface of the food product using the distance sensor, directing a jet of pressurized fluid to apply a force to a position on the surface of the food product, wherein the jet of pressurized fluid is configured to provide a deformation of the surface of said food product, and wherein the distance sensor measures the distance between the device and the surface of the food product at the position of the deformation of the surface of the food product due to the applied force and/or due to the removal of said applied force.

Accordingly, the method according to the present invention applies a force to the position on the surface of a product by directing a jet of pressurized fluid to said position on the surface. In addition, the device comprises a distance sensor which measures the distance between the device and the position of the surface, in particular at the position of the surface where the jet of pressurized fluid impinges on the surface of the product. Any deformation of the surface at said position where the jet of pressurized fluid is directed to is measured by the distance sensor.

Such a method is particularly advantageous for analyzing deformable products, such as dough products. Because of the viscosity and elasticity of dough, the surface of the dough will develop a deformation due to the applied force, and this deformation will at least partially disappear when the force is removed from said surface of the dough. The method of the present invention allows to monitor the development and/or removal of the deformation by means of the distance sensor. From said development and/or removal of the deformation of the surface by the jet or pressurized fluid, a measure of material properties such as viscosity and elasticity, can be determined, for example by fitting the data to a mathematical visco-elastic deformation model.

Preferably, the development and/or removal of the deformation of the surface of the product as measured by the distance sensor is analyzed by a real-time electronic processing system, which is configured for real-time fitting the data to said mathematical visco-elastic deformation model, and which provides a substantially real-time output of the material properties.

In an embodiment, the distance sensor measures the distance between the device and the position of the surface where the jet of pressurized fluid is directed to.

In an embodiment, the distance sensor acquires a series of measurements when said jet of pressurized fluid applies a force to the position on the surface of the product.

In an embodiment, the product, such as a lump of dough, comprises a deformable product, wherein the distance sensor measures the distance between the device and the position of the surface where the jet of pressurized fluid is directed to.

In an additional or alternative embodiment, the product is covered by a liquid coating, wherein the jet of pressurized fluid pushes away said liquid coating at the position on the surface of the product, wherein the distance sensor measures the distance between the device and the position of the surface where the jet of pressurized fluid is directed to, preferably before and during the jet of pressurized fluid pushes away said liquid coating. By measuring the distance before or after the jet of pressurized fluid pushes away said liquid, and during the jet of pressurized fluid pushes away said liquid, a measure of the thickness of said liquid coating can be obtained. In addition, by monitoring how the liquid is pushed away as a function of time, a measure for the viscosity of said liquid can be obtained.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an exemplary embodiment shown in the attached drawings, in which:

FIG. 7 shows a schematic view of a fourth example of a device according to the present invention arranged in an assembly for processing of said products.

DETAILED DESCRIPTION OF THE INVENTION

Figure 1:
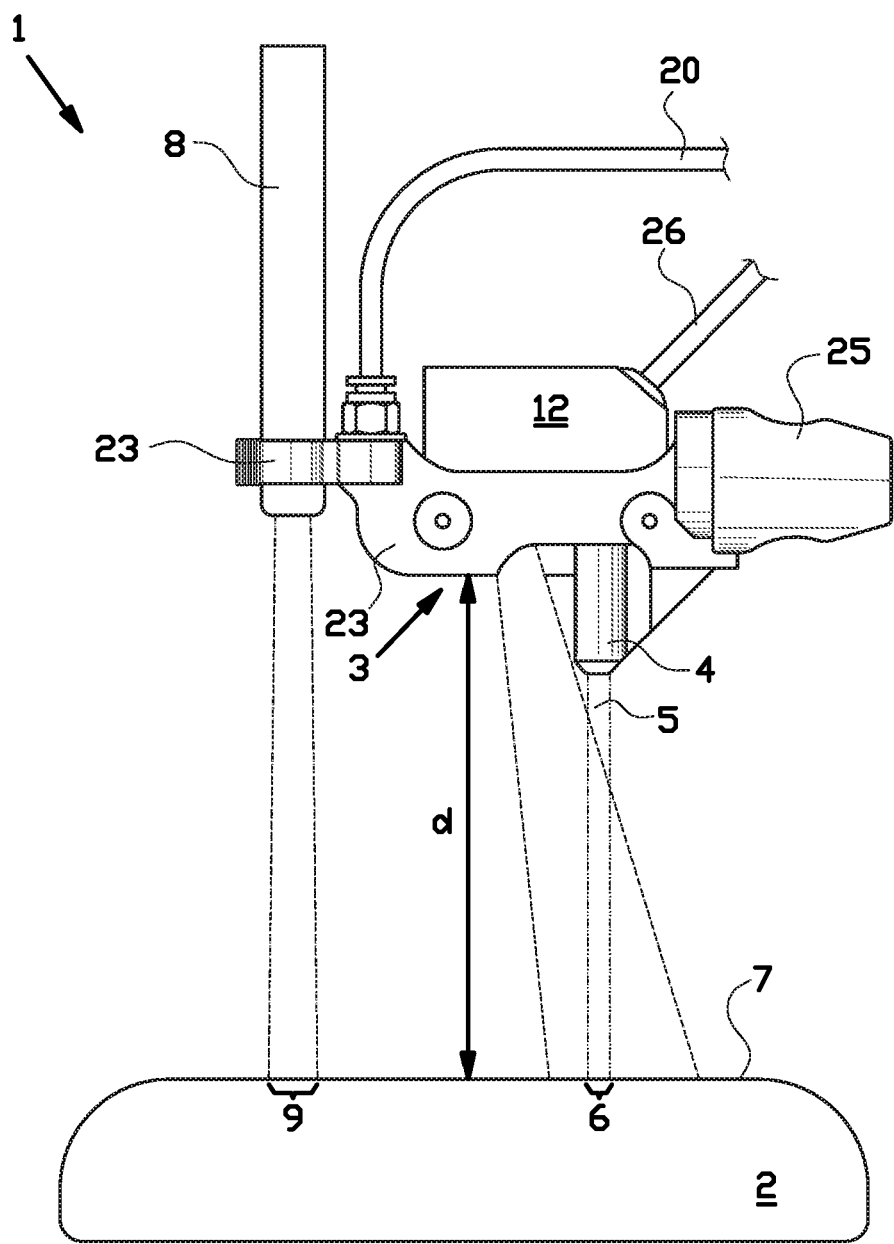
FIG. 1 shows a schematic side view of a first example of a device according to the present invention.

FIG. 1 shows a schematic side view of a first example of a device 1 for a contactless analysis of a product 2, in particular a food product such as a lump of dough. Said device 1 comprises a distance sensor 3 configured for measuring a distance d between the device 1 and the product 2. Furthermore, said device 1 comprises a nozzle 4 configured for directing a jet 5 of pressurized fluid to a position 6 on a surface 7 of said product 2. Said device 1 also comprises a temperature sensor 8, in particular an infra-red temperature sensor for sensing the temperature on a temperature measurement position 9 on the surface 7 of the product 2, which temperature measurement position 9 is arranged spaced apart from the position 6 where the jet 5 of pressurized fluid impinges on the surface 7 of said product 2.

Figure 2A:
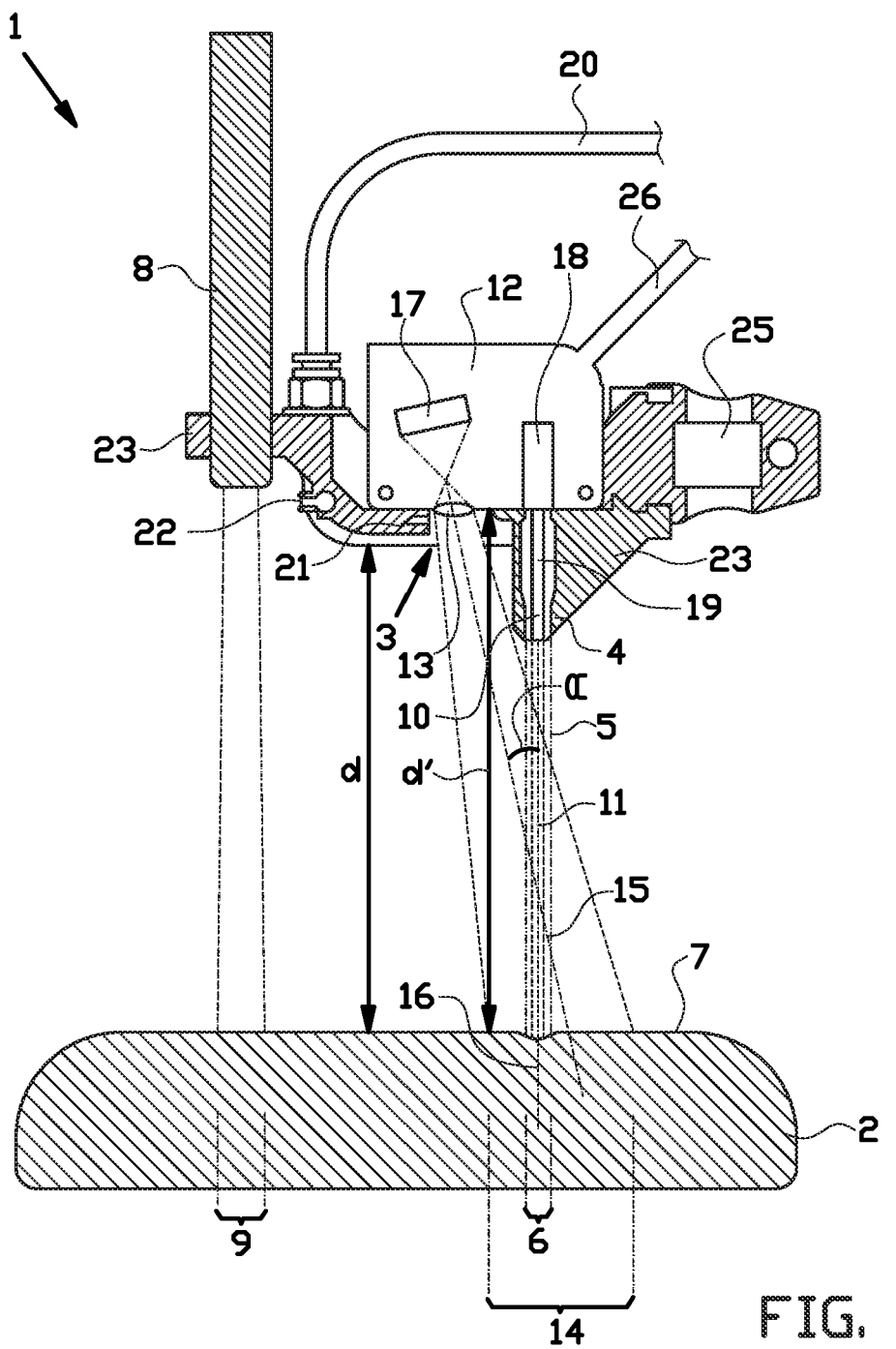
FIG. 2A shows a schematic cross-section of the device of FIG. 1.

As schematically shown in the cross-section of FIG. 2A, the distance sensor 3 comprises an illuminating beam source 10 for projecting a light beam 11 at least to the position 6 on the surface 7 of the product. In this embodiment, the illumination beam source 10 comprises an light emitter 18, for example a lamp, LED or Laser, which emits a light beam. The light beam passes substantially centrally through the nozzle 4 via light delivering member 19, such as a tube or waveguide, and exits said light delivering member 19 at or near the output of the nozzle 4. Accordingly, the illuminating beam source 10 is configured for projecting the light beam 11 along a central axis 16 of the jet 5 of pressurized fluid from the nozzle 4.

In addition the distance sensor 3 comprises a light collecting unit 12 for receiving light reflected from said surface 7 of the product 2. The light collecting unit 12 is configured for providing a measure of the distance d' between the light collecting unit 12 and the position 6 on the surface 7 of the product 2 where the light beam 11 impinges on said surface 7. In particular, the light collecting unit 12 comprises one or more lenses 13 for projecting and/or imaging a detection area 14 on said surface 7 of the product 2 on a light sensor 17 inside said light collecting unit 12. Preferably this light sensor 17 comprises a CCD sensor array.

A schematically shown in FIG. 2A, the one or more lenses 13 are configured such that an optical axis 15 of the one or more lenses 13 is arranged at a sharp angle α to an optical axis 16 of the light beam 11. In particular the optical axis 15 is arranged to intersect the light beam 11 at a distance and spaced apart from the device 1. Accordingly, the position 6 of the light spot in the image on the light sensor 17 will move over the light sensor 17 as a function of the distance d between the device 1 and the surface 7 of the product 2.

The device 1 further comprises a supply tube 20 for supplying said fluid to the device. The supply tube 20 is connected to the nozzle 4 to provide said pressurized fluid to the area inside the nozzle 4 and around the light delivering member 19. The pressurized fluid exits the nozzle 4 to provide the jet 5 of pressurized fluid towards the product 2.

The device 1 is provided with a first branch for providing at least part of said fluid from the supply tube 20, via a first fluid output 21 to the light collecting unit 3, in particular to the lens 13. The pressurized fluid from the first fluid output 21 is arranged to blow away any dust from the lens 13, and substantially prevents contamination and/or the clogging up of the lens 13.

The device 1 is further provided with a second branch for providing at least part of said fluid from the supply tube 20, via a second fluid output 22 to the temperature sensor 8. The pressurized fluid from the second fluid output 22 is arranged to blow away any dust from the temperature sensor 8, and substantially prevents contamination and/or the clogging up of the temperature sensor 8.

It is noted that the first fluid output 21 and/or the second fluid output 22 may also be connected to a dedicated second supply tube (not shown) for providing a dedicated cleaning fluid. An advantage of such a dedicated second supply tube is, that the delivery of cleaning fluid can be independent of the delivery of fluid through the nozzle 4.

The device 1 further comprises a mounting member 23 for holding the various components of the device 1. Preferably the mounting member 23 is provided with a connector 25 for mounting the device 1 to a frame of an assembly for processing products.

Figure 2B:
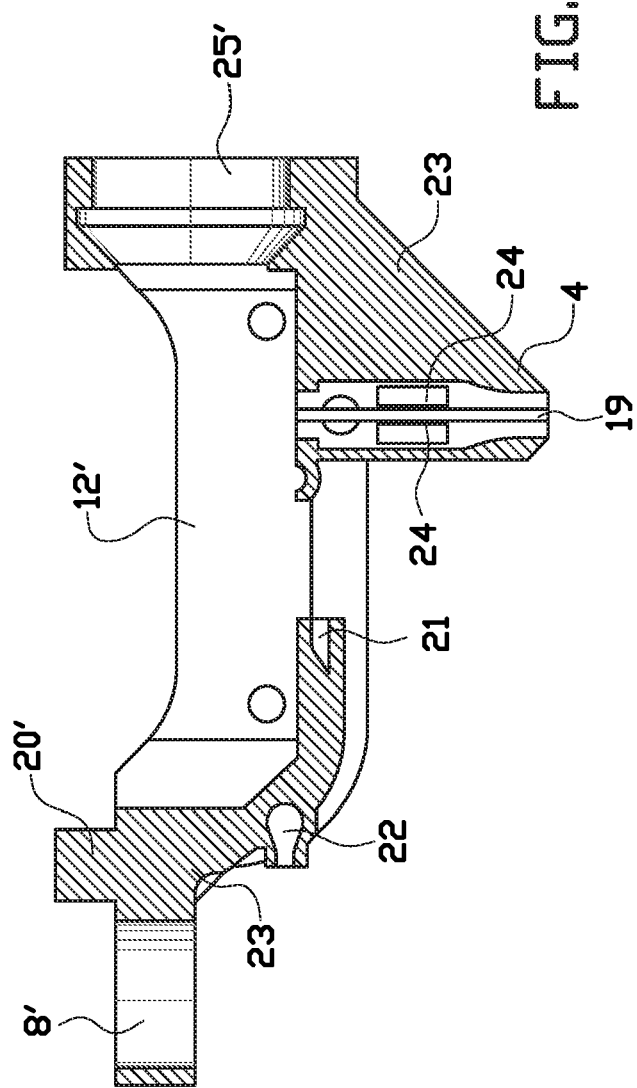
FIG. 2B shows a detail of the schematic cross-section of FIG. 2A.

FIG. 2B schematically shows the mounting member 23 which comprises a connector 20' for connecting the supply tube 20 and an integral tubing for providing a fluid connection between the connector 20' and the nozzle 4. The integral tubing also comprises said first and second branch for providing part of the fluid from the supply tube 20 to the first fluid output 21 and second fluid output 22. The mounting member 23 further comprises a distance sensor mounting position 12', a temperature sensor mounting position 8' and a connector mounting position 25'.

It is noted that in this example, the nozzle 4 is substantially integrally formed with the mounting member 23. The nozzle 4 can be provided with one or more jet vectoring members 24, which are arranged inside said nozzle 4 and surrounding said light delivery member 19. In an simple embodiment, the one or more jet vectoring members 24 comprises a series of substantially parallel tubes which extend in a direction substantially parallel to a central axis of the jet.

Figure 3:
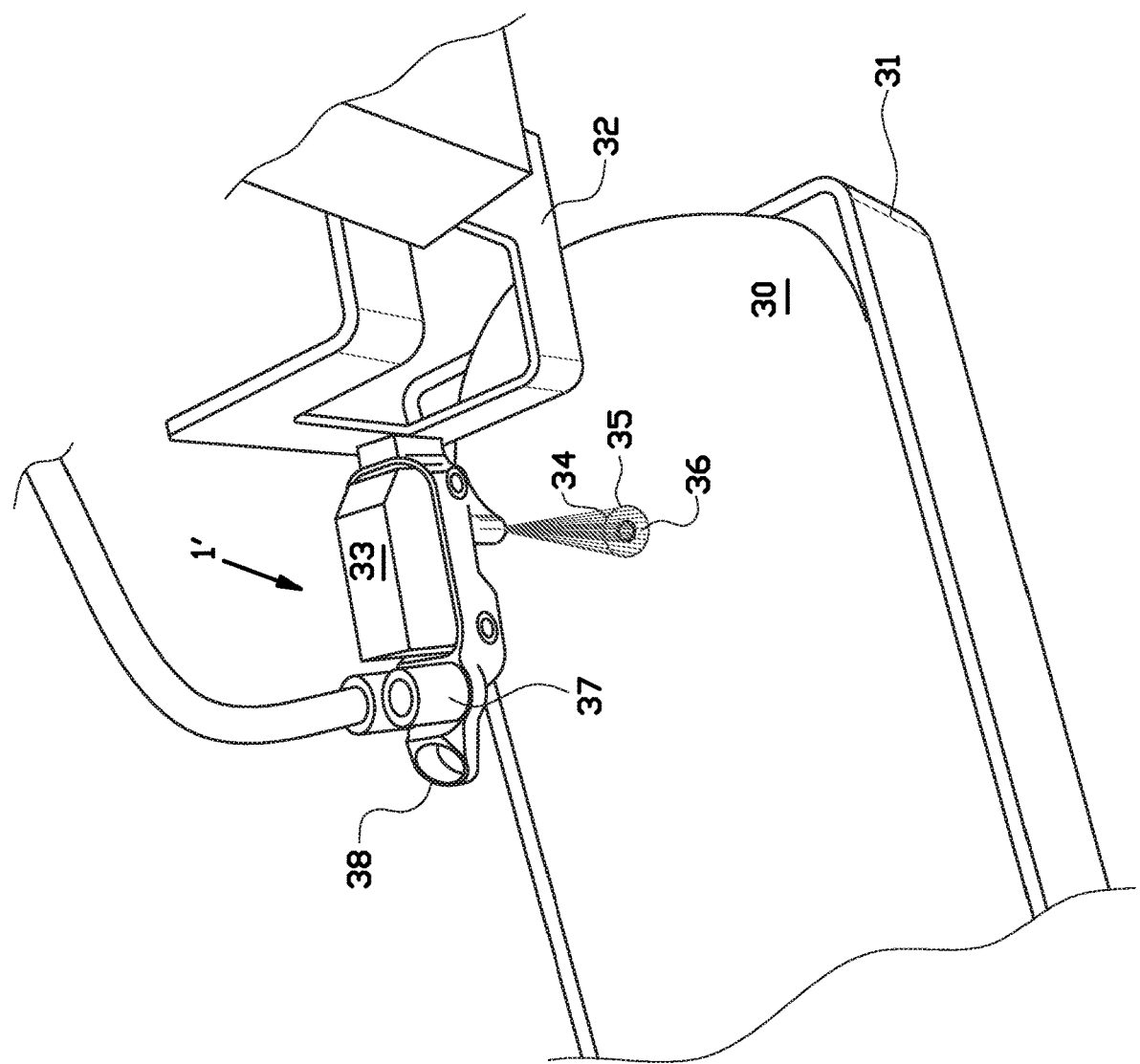
FIG. 3 shows a schematic view of the device of FIG. 1 arranged in an assembly for the production of dough products.

FIG. 3 shows the device 1 of FIG. 1 arranged in an assembly for the production of dough products, in particular for the production of bread. In this example the lump of dough 30 for making the bread is arranged in a bread pan 31. It is noted that in a suitable production environment, multiple bread pans are arranged in a baking tray, and multiple baking trays are arranged in series to travel one behind the other through the various stations of the assembly.

The device 1 is mounted to a frame 32 which frame 32 is arranged at a fix position along the assembly for producing dough products. When performing a measurement, the bread pans are temporarily held at a fixed position with respect to the device 1. This may be done by temporarily moving the device 1 substantially synchronous with the bread pan 31 or by temporarily stopping the bread pen 31 at the location of the device 1.

In order to perform a measurement, the distance sensor 33 measures the distance between the device 1' and the surface of the dough 30. For measuring the distance, a light beam 34 is projected onto the surface of the dough 30. A light collecting unit inside said distance sensor 33 as describe with reference to FIG. 2A, is configured for receiving light reflected from said surface of the dough 30. The light collecting unit is configured for providing a measure of the distance between the light collecting unit and the position on the surface of the product where the light beam impinges on said surface.

Figure 4:
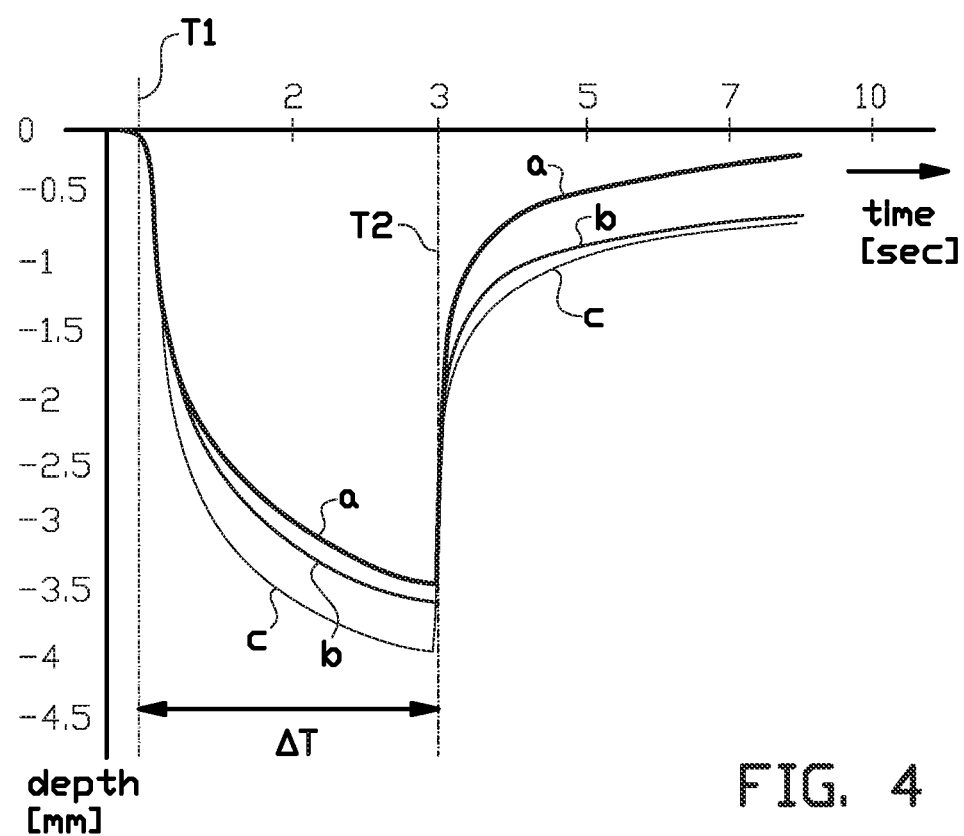
FIG. 4 shows a schematic presentation of examples of measurements of the distance between the device and the position of the surface where the jet of pressurized fluid is directed to as a function of time.

Subsequently a jet 35 of pressurized fluid, in particular pressurized air, is activated to apply a force to an area 36 on the dough 30. Due to said force, the dough 30 will be slightly compressed in said area 36, which results in an increase in the distance between the dough 30 and the distance sensor 33. FIG. 4 schematically shows the development of the compression in the area 36 of the dough 30 as a function of time. At time T1 the jet 35 of pressurized air is activated, and the graphs a, b, c show the development of a depression in the dough 30 as a function of time. At time T2 the jet 35 of pressurized air is stopped, and the graphs a, b, c show the decrease or removal of the depression in the dough 30 as a function of time. Accordingly the jet 35 of pressurized air acts on the dough 30 during a time interval ΔT of approximately 2 seconds (in this particular example). The distance sensor 33 measures the development of the deformation of the surface of the product 30 due to the applied force by the jet 35 and/or the removal of the deformation of the surface of the product 30 after the removal of said applied force.

The various graphs a, b, c represent example measurements on different types of dough; in particular doughs with a different viscosity and/or elasticity. From these graphs a, b, c, and in particular from one or more measurement points of said graphs a, b, c, a measure for the viscosity and/or elasticity of the individual dough types can be determined.

In particular by measuring the decrease or removal of the deformation of the surface of the food product 30 after the deformation of the surface by the jet 35, is highly suitable to perform the measurement on a moving food product, using a nozzle for directing the jet of fluid onto the moving food product at a fixed position along a food production line, and to measure the decrease or removal of the deformation of the surface of the food product downstream of the fixed position of the nozzle.

It is noted that the depression in de dough 30 due to the jet 35 of air will decrease when the jet 35 of pressurized fluid is stopped, and in time the dough will substantially move back to its original shape. Accordingly, the position where the measurement has been performed is at least substantially invisible in the final product.

It is further noted that the size of the depression in the dough 30 is small with respect to the size of the product. Typically, the depression has a diameter of about 5 or 6 mm and a depth of 3 to 5 mm.

It is further noted, that the device 1' according to this example comprises a second connector for connecting a supply tube for cleaning fluid (not shown), and a temperature sensor mounting position 38.

Figure 5:
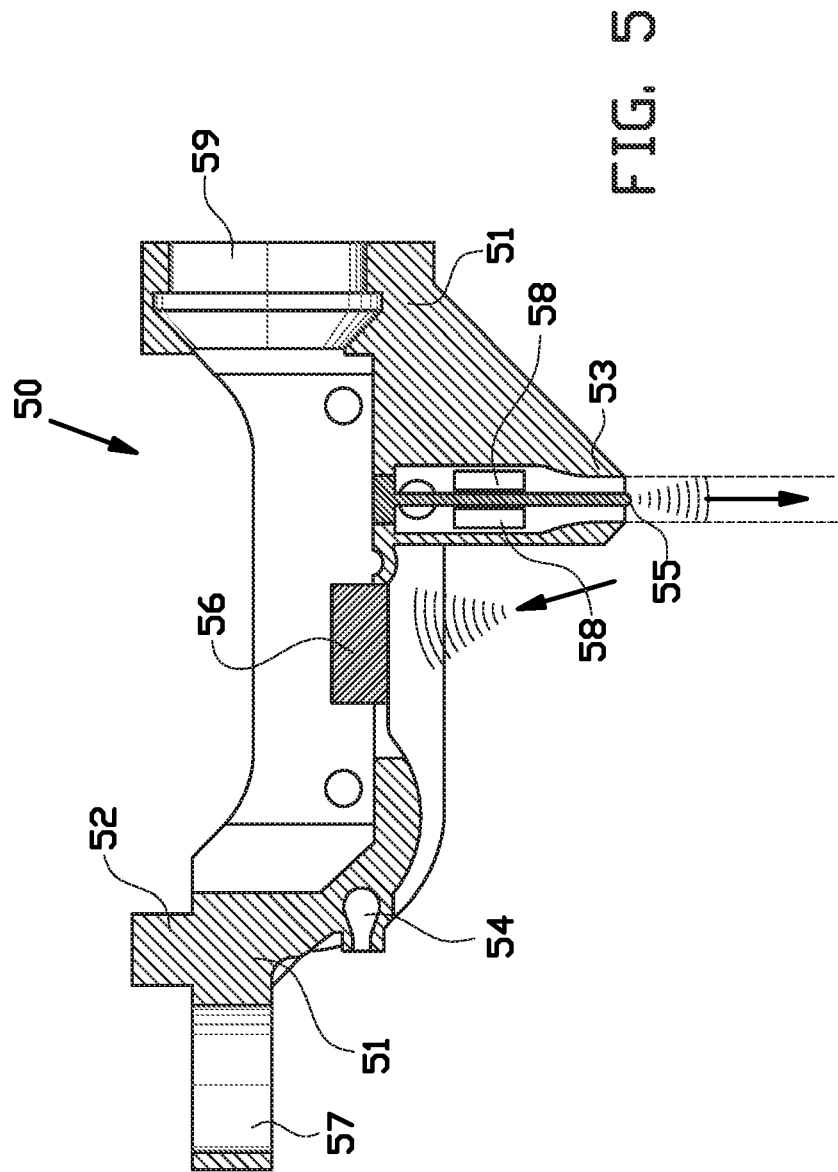
FIG. 5 shows a schematic cross-section of a second example of a device according to the present invention.

FIG. 5 shows a schematic cross-section of a second example of a device according to the present invention. The device essentially uses the same mounting member 51 as shown in FIG. 2B (which is not essential for this embodiment) and comprises a connector 52 for connecting the supply tube and an integral tubing for providing a fluid connection between the connector 52 and the nozzle 53. The integral tubing also comprises a branch for providing part of the fluid from the connector 52 to the fluid output 54 for providing a cleaning fluid to a temperature sensor (not shown) which may be mounted in the temperature sensor mounting position 57. In addition the mounting member 51 comprises a connector mounting position 59 for attaching a connector for connecting the mounting member 51.

The device 50 comprises an ultrasonic sensor comprising at least a transmitter 55 and a receiver 56. The transmitter 55 is at least partially arranged in the nozzle 53, preferably substantially in the center of said nozzle 53.

It is noted that also in this example, the nozzle 53 is substantially integrally formed with the mounting member 51. The nozzle 53 is provided with one or more jet vectoring members 58, which are arranged inside said nozzle 53 and surrounding said transmitter 55. In an simple embodiment, the one or more jet vectoring members 58 comprises a series of substantially parallel tubes which extend in a direction substantially parallel to a central axis of the nozzle 53.

Figure 6A:
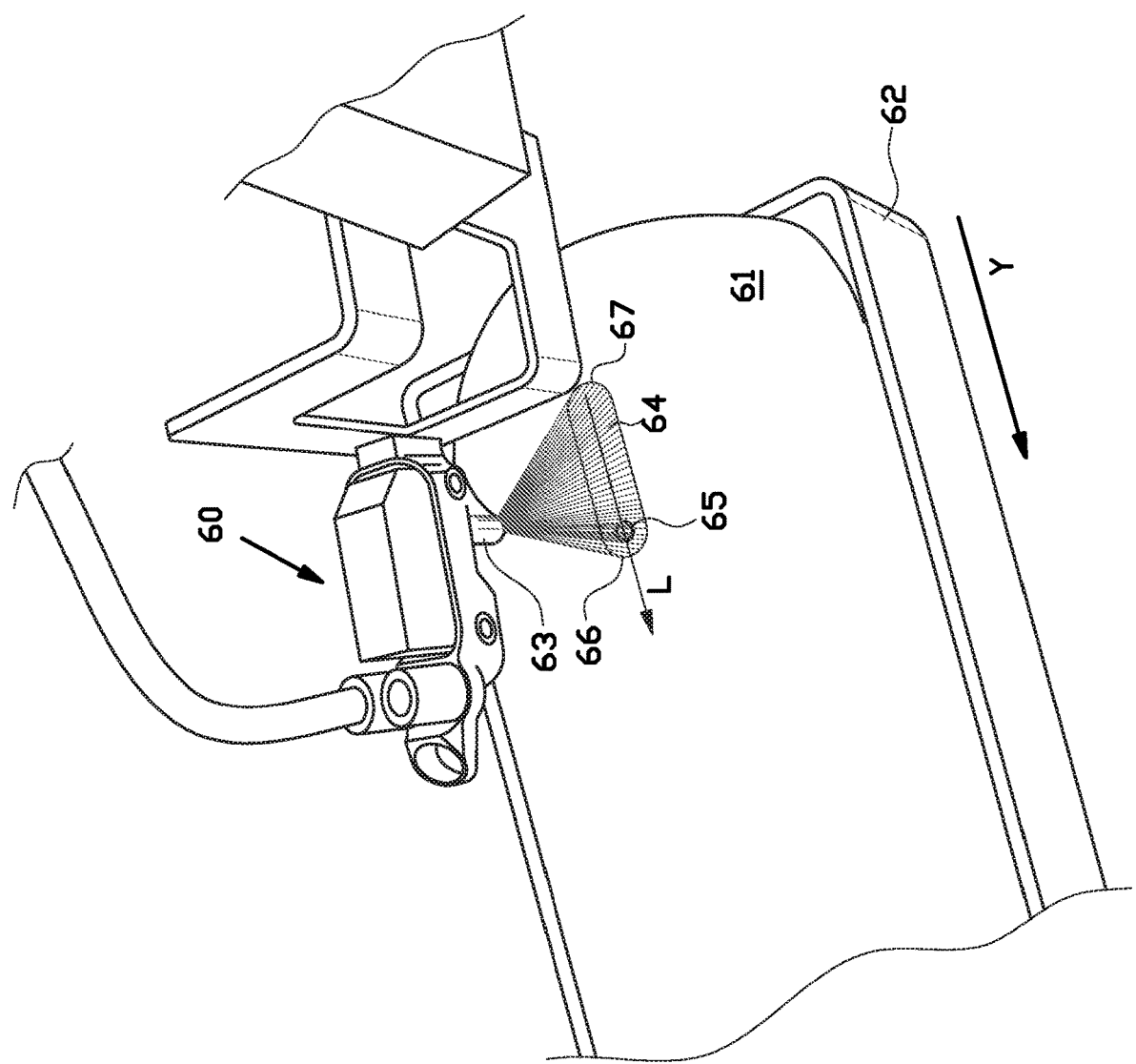
FIG. 6A shows a schematic view of a third example of a device according to the present invention arranged in an assembly for processing of said products.

FIG. 6A shows a schematic view of a third example of a device 60 according to the present invention arranged in an assembly for processing products. The assembly comprises a conveying apparatus for conveying the products, in particular lumps of dough 61 in a baking pan 62, in a conveyance direction Y in the assembly, and wherein the device 60 comprises a nozzle 63 for producing a jet 64 of pressurized fluid with an elongated cross-section, as schematically indicated in FIG. 6. The nozzle 63 is arranged such that a longitudinal direction L of said jet 64 with elongated cross-section is arranged substantially parallel to the conveyance direction Y. The distance sensor is arranged so that the light beam 65 is positioned at or near an upstream end 66 of the jet 64 with elongated cross-section, at least in the longitudinal direction of the jet 64 and with respect to the conveyance direction Y.

When the baking pan 62 with the dough 61 moves along the conveyance direction Y, and the device 60 is arranged substantially at a fixed position, the jet 64 with elongated cross-section is scanned over the surface of the dough 61. The part of the dough at the upstream end 66 experience the force of the jet 64 only for a short moment in time, whereas the part of the dough at the downstream end 67 travels along the conveyance direction Y and experiences the force of the jet 64 all the time this part is below the jet 64 with elongated cross-section. During this travel, the deformation of the dough develops substantially similar as shown in the graphs in FIG. 4. Accordingly, by measuring the distance at the fixed position at the upstream end of the jet 64 with elongated cross-section and as a function of time, the development of the deformation of the surface of the dough 61 due to the jet 64 can be measured on a traveling product.

Figure 6B:
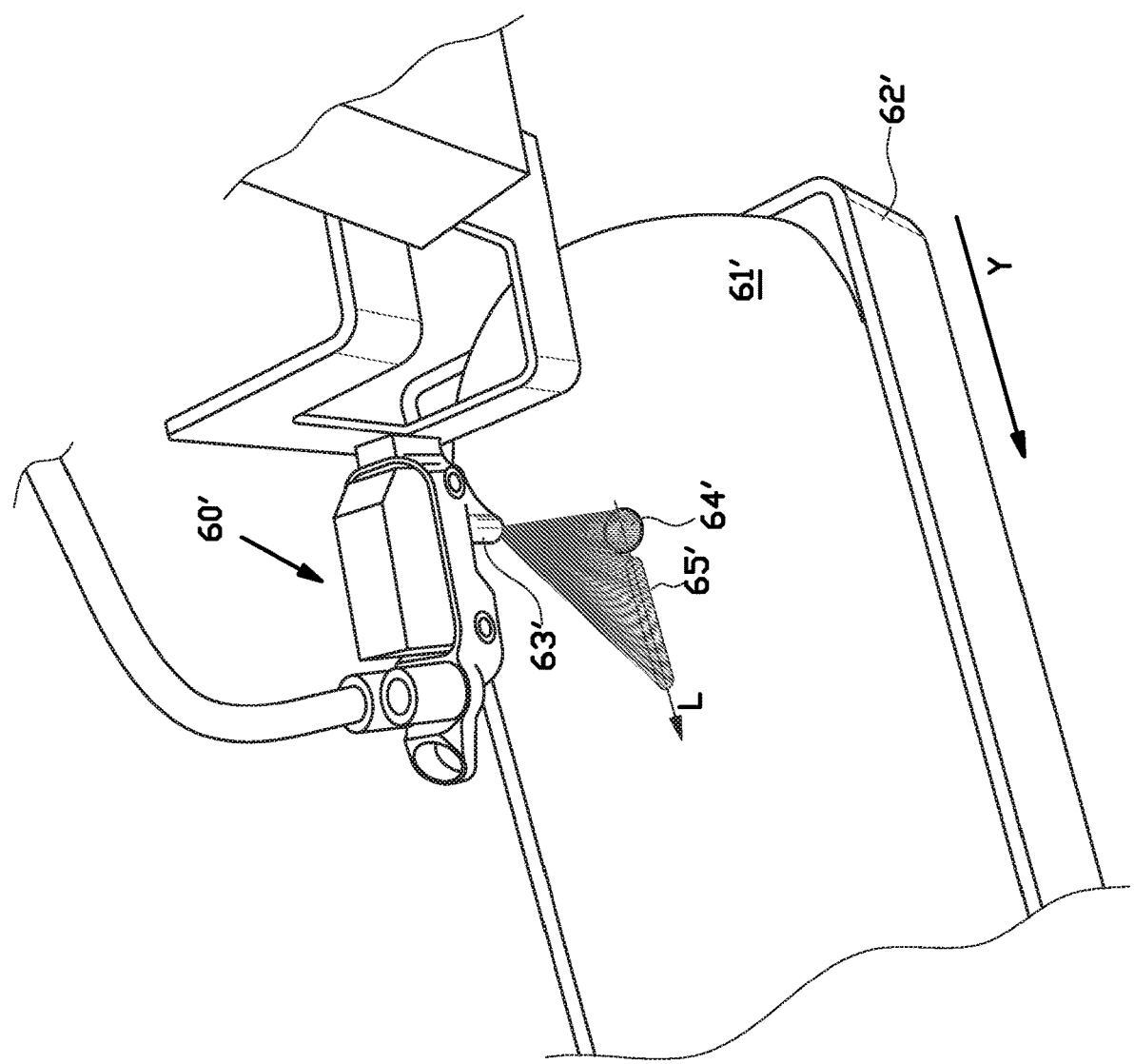
FIG. 6B shows a schematic view of an alternative example of a device according to the present invention arranged in an assembly for processing of said products.

Alternatively, FIG. 6B shows a schematic view of an example of a device 60' according to the present invention arranged in an assembly for processing products. The assembly comprises a conveying apparatus for conveying the products, in particular lumps of dough 61' in a baking pan 62', in a conveyance direction Y in the assembly, and wherein the device 60' comprises a nozzle 63' for producing a jet 64' of pressurized fluid with an round cross-section, as schematically indicated in FIG. 6B.

The distance sensor is arranged so that the light beam 65' is positioned downstream of the jet 64', at least in the longitudinal direction of the jet 64 and with respect to the conveyance direction Y.

When the baking pan 62' with the dough 61' moves along the conveyance direction Y, and the device 60' is arranged substantially at a fixed position, the jet 64' provides a deformation of the surface of the dough 61 at said fixed position. Downstream of this position the jet 64' no longer deforms the surface of the dough 61' and the deformation decreases due to the elastic properties of the dough 61'. This decrease or removal of the deformation, downstream of the fixed position of the jet 64' is monitored by the distance sensor using the light beam 65'. Accordingly, during the travel of the dough 61' in the direction Y, the deformation of the dough decreases substantially similar as shown in the graphs in FIG. 4 after the time interval ΔT. Accordingly, by measuring the distance at various positions downstream of the jet 64' and/or as a function of time, the decrease or removal of the deformation of the surface of the dough 61' due to the jet 64' can be measured on a traveling product, in particular without the need of moving the device 60' along with the traveling product.

It is noted that the distance sensor in this example can also be separate and arranged downstream from the nozzle 63', for example configured to project a line shaped light beam 65' or a laserline on the surface of the dough 61' downstream of the position of the jet 64', and comprising a camera and an image analysis processor which is configured to analyze a deformation of said line of light due to the decrease or removal of the deformation of the surface of said dough 61' by the jet 64' of compressed fluid.

FIG. 7 shows a schematic view of a fourth example of a device 70 according to the present invention arranged in an assembly for processing of said products. The assembly comprises a conveying apparatus for conveying the products, in particular lumps of dough 71 in a baking pan 72, in a conveyance direction Y in the assembly. The device 70 comprises a nozzle 73 for producing a jet 74 of pressurized fluid with an elongated cross-section, as schematically indicated in FIG. 7. The nozzle 73 is arranged such that a longitudinal direction L of said jet 74 with elongated cross-section is arranged substantially parallel to the conveyance direction Y. The distance sensor is configured to provide an elongated light beam 75. The elongated light beam 75 is arranged such that a longitudinal direction L of said light beam 75 is arranged substantially parallel to the conveyance direction Y and substantially in the center of the jet 74 with elongated cross-section.

When the baking pan 72 with the dough 71 moves along the conveyance direction Y, and the device 70 is arranged substantially at a fixed position, the jet 74 with elongated cross-section is scanned over the surface of the dough 71. The part of the dough at the upstream end 76 experience the force of the jet 74 only for a short moment in time, whereas the part of the dough at the downstream end 77 travels along the conveyance direction Y and experiences the force of the jet 74 all the time this part is below the jet 74 with elongated cross-section. During this travel, the deformation of the dough develops substantially similar as shown in the graphs in FIG. 4. When the jet 74 has been applying force to the surface of the dough 71 for a certain amount of time in which the part of the dough at the downstream end 77 has traveled to the upstream end 76, the deformation of the surface of the dough 71 represents the development of the deformation along the length of the jet 74; at the downstream end 77 the force starts to be applied and at the upstream end 78 the force has been applied during the time of traveling from the downstream end to the upstream end. Accordingly, by measuring the distance at several positions along the elongated light beam 75, the complete development of the deformation of the dough due to the jet 74 can be acquired with substantially one moment of measurement, for example by using a camera to image the elongated light beam 75 and using image analysis processor for retrieving distance information for the distortion of the light beam 75 due to the deformation of the surface of the dough 71. Accordingly, the development of the deformation of the surface of the dough 71 due to the jet 74 can be measured in one measurement and/or on a traveling product.

Figure 8:
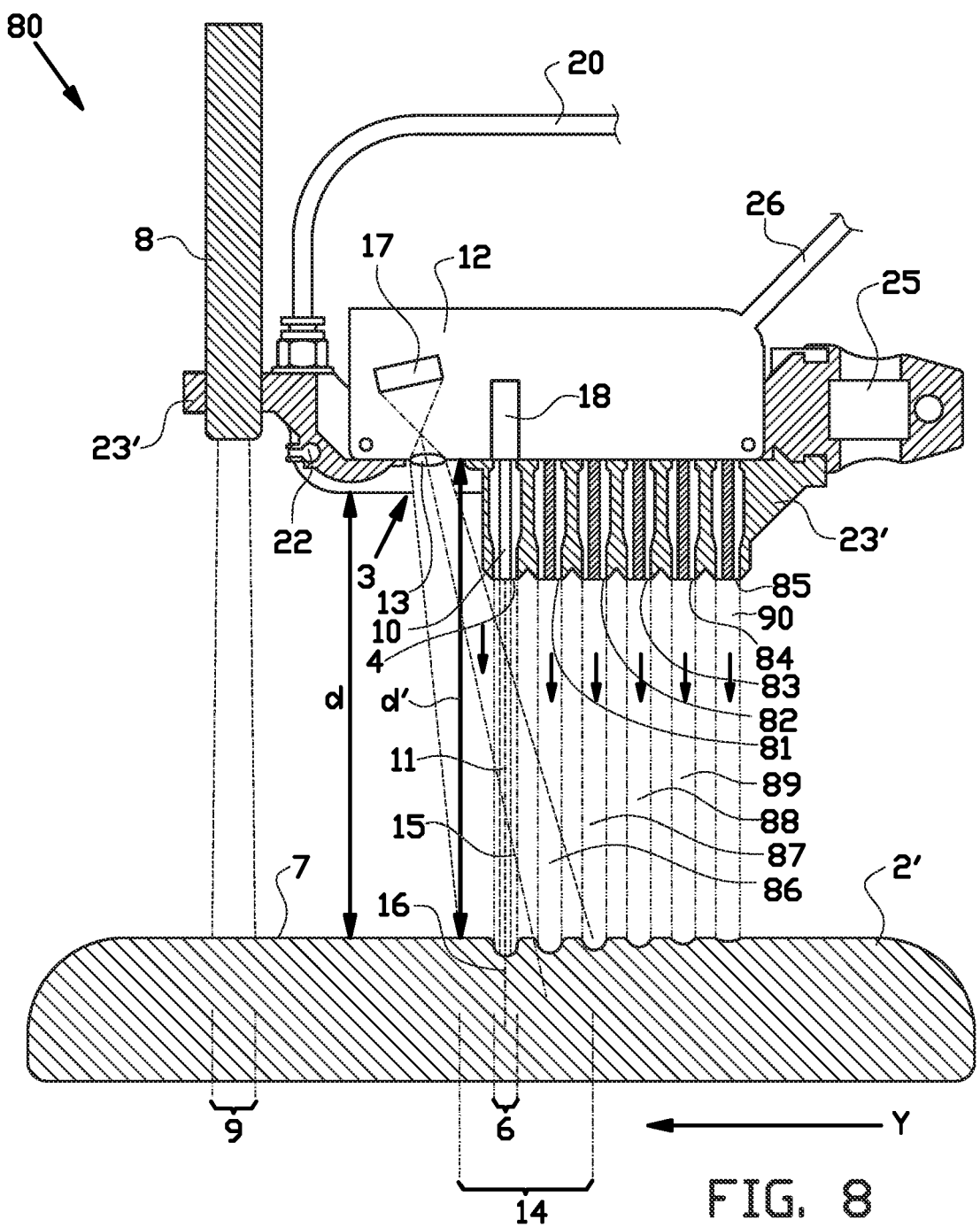
FIG. 8 shows a schematic view of a fifth example of a device according to the present invention arranged in an assembly for processing of said products.

FIG. 8 shows a schematic view of a fifth example of a device 80 according to the present invention arranged in an assembly for processing of said products. It is noted that the device 80 is similar to the first example shown in FIG. 2A, but differs in that the device comprises a series of nozzles 4, 81, 82, 83, 84, 85 each one for producing a jet 5, 86, 87, 88, 89, 90 of pressurized fluid, wherein said series of nozzles are arranged on a line.

The assembly comprises a conveying apparatus for conveying the products, in particular lumps of dough 2', in a conveyance direction Y in the assembly. The nozzles 4, 81, 82, 83, 84, 85 are arranged one behind the other is a longitudinal direction L substantially parallel to the conveyance direction Y. The distance sensor 12 is arranged so that the light beam 11 is positioned in the most upstream nozzle 4 with respect to the conveyance direction Y.

When the dough 2' moves along the conveyance direction Y, and the device 80 is arranged substantially at a fixed position, the series of jets 5, 86, 87, 88, 89, 90 are scanned over the surface 7 of the dough 2'. The part of the dough at the upstream jet 5 experience the force of the jet 5 only for a short moment in time, whereas the part of the dough at the downstream jet 90 travels along the conveyance direction Y and experiences the accumulated force of the series of jets 5, 86, 87, 88, 89, 90. During this travel, the deformation of the dough surface 7 develops substantially stepwise but in general similar as shown in the graphs in FIG. 4. Accordingly, by measuring the distance at the fixed position at the upstream jet 4 and as a function of time, the development of the deformation of the surface 7 of the dough 2' due to successive application of a force on the dough 2' by the jets 5, 86, 87, 88, 89, 90 can be measured on a traveling product.

Figure 9A:
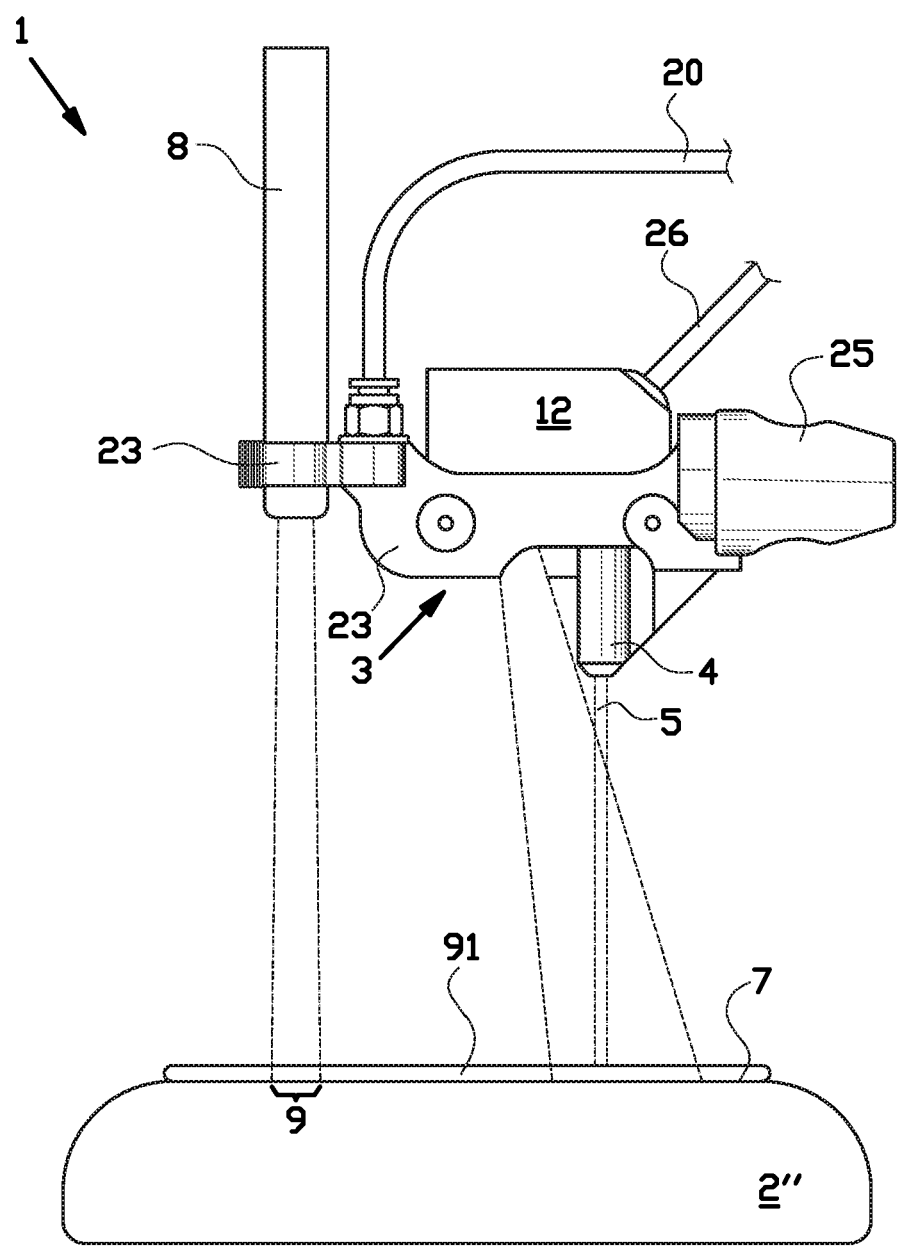
FIGS. 9A and 9B show a schematic view of an application of the device of FIG. 1 for analyzing liquid coatings on a substantially solid carrier.
Figure 9B:
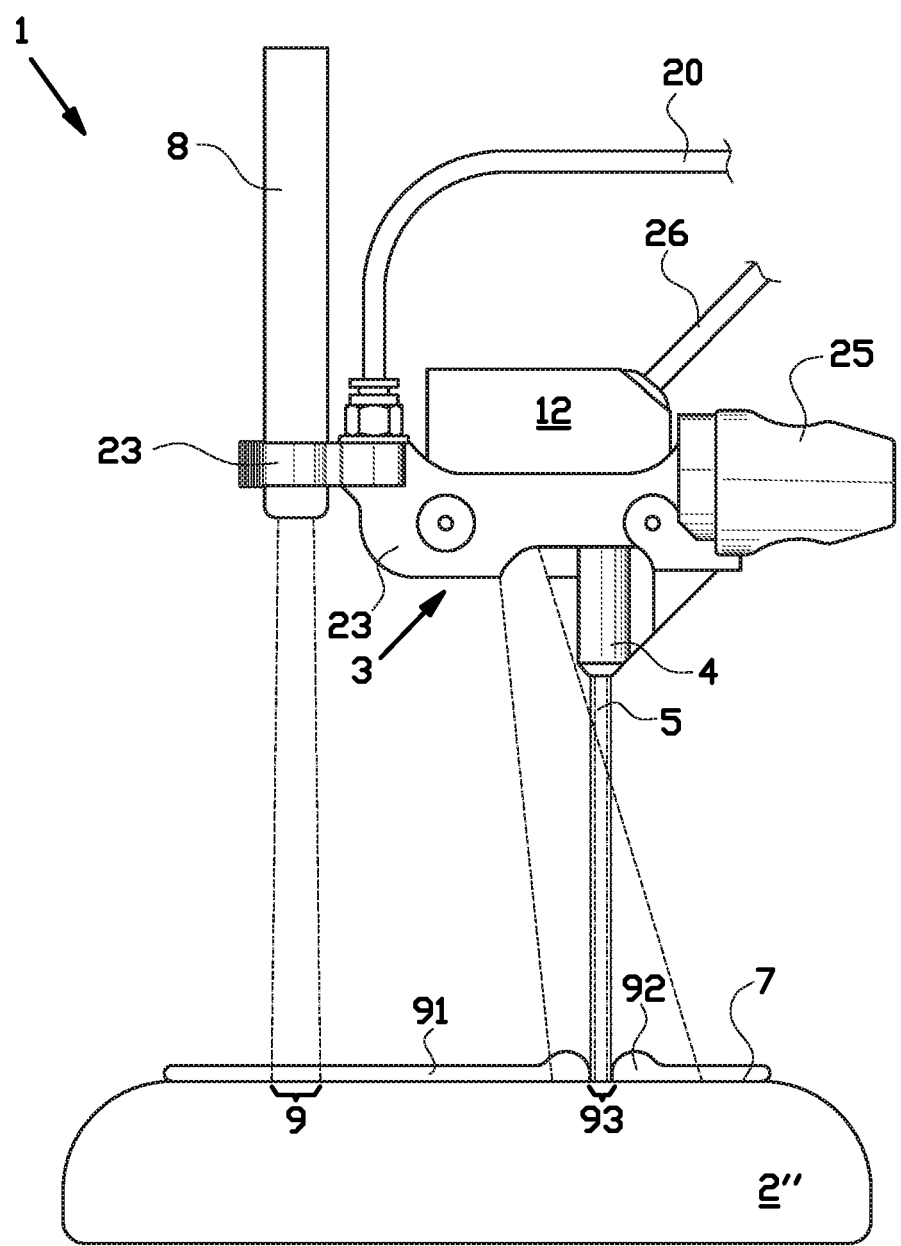

FIGS. 9A and 9B show a schematic view of an application of the device of FIG. 1 for analyzing liquid coatings 91 on a substantially solid carrier 2". When the carrier 2" is covered by a liquid coating 91, the distance sensor 3 can measure the distance between the device 1 and the upper surface of the liquid coating 91, as schematically shown in FIG. 9A.

Subsequently, the jet 5 of pressurized fluid is activated. The jet 5 of pressurized fluid is configured to push away said liquid coating 91 at the position 93 on the surface 7 of the carrier 2". Accordingly, the distance sensor 3 measures the distance between the device 1 and the surface 7 of the carrier 2", as schematically shown in FIG. 9B. Accordingly the thickness of the liquid coating 91 can be determined from the distance measurements before and during the jet 5 of pressurized fluid pushes away said liquid coating 91.

In addition, by monitoring how the liquid coating 91 is pushed away as a function of time, and or by analyzing any accumulation of liquid 92 around the jet 5, information about the viscosity of the liquid coating 91 can be obtained.

It is noted that the carrier 2" may be a solid carrier for measuring the properties of the liquid coating. The carrier 2" may also comprise a lump of dough with a coating of rice paste for the manufacturing of Tiger bread or Giraffe bread. In the latter case, the pressure of the jet 5 is carefully adjusted to push the rice past away, and not to provide an imprint on the dough.

Figure 10:
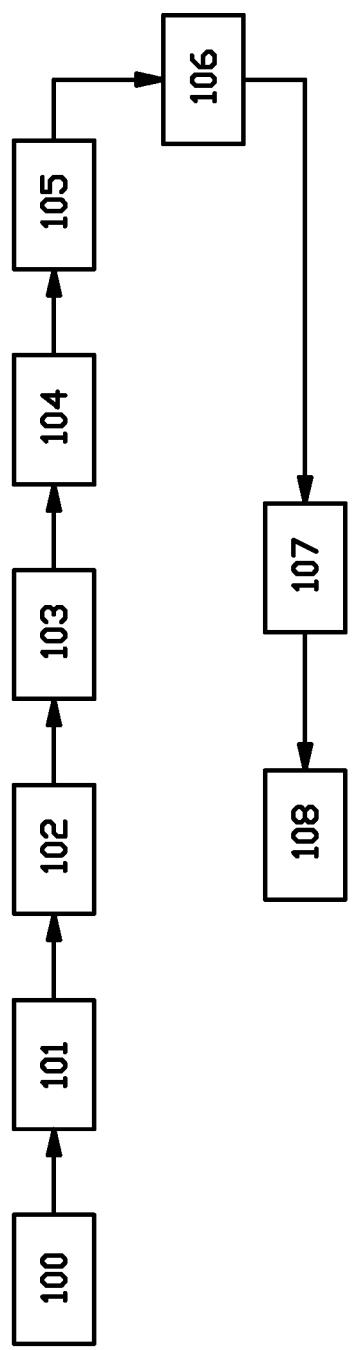
FIG. 10 shows a schematic example of various steps in a production line for dough products.

FIG. 10 shows a schematic example of various steps in a production line for dough products. The industrial production of bread comprises the steps of mixing the components 100, kneading the dough 101, dividing the dough 102, forming or rounding the dough 103, proofing 104, baking the dough 105, de-panning the bread (in case the bread is baked in a baking pan) 106, cooling and/or freezing the bread 107, and packing the bread 108. The device of the present invention can be used to monitor the dough at various process steps, in particular immediately after the various components have been mixed to form the dough, until just before the dough goes into the oven for baking the bread.

It is to be understood that the above description is included to illustrate the operation of the preferred embodiments and is not meant to limit the scope of the invention. From the above discussion, many variations will be apparent to one skilled in the art that would yet be encompassed by the scope of the present invention.

In summary, the invention relates to a device and a method for a contactless analysis of a product, in particular for the contactless analysis of a dough product. The device comprises a distance sensor configured for measuring a distance between the device and the product, and a nozzle configured for directing a jet of pressurized fluid to a position on a surface of said product. The distance sensor is arranged for measuring the distance between the device and the position of the surface where the jet of pressurized fluid is directed to. Preferably, the distance sensor is at least partially arranged in the nozzle, preferably substantially in the center of said nozzle.

The invention claimed is:

1. A device for performing an analysis of a dough product, said device comprising:
    a distance sensor configured for contactless measuring a distance between the device and a surface of the dough product, and
    a nozzle configured for directing a jet of pressurized fluid to a position on the surface of said dough product, wherein the jet of pressurized fluid is configured for providing a deformation of the surface of said dough product,
    wherein the distance sensor is arranged for measuring the distance between the device and the position on the surface of the dough product where the jet of pressurized fluid is and/or has been directed to for monitoring a development and/or a decrease or removal of the deformation of the surface of said dough product,
    wherein the distance sensor includes
        an illuminating beam source for projecting a light beam at least to the position on the surface of the dough product, and
        a light collecting unit for receiving light reflected from said surface of the dough product, wherein the light collecting unit is configured for providing a measure of the distance between the light collecting unit and the position on the surface of the dough product where the light beam impinges on said surface, and
    wherein the device further includes
        a supply tube for supplying said fluid, wherein said supply tube comprises a first branch for providing at least part of said fluid in the supply tube to the light collecting unit,
        or
        a first supply tube for supplying said fluid, and a second supply tube for supplying a cleaning fluid to the light collecting unit.

2. The device according to claim 1, wherein the distance sensor is partially arranged in the nozzle.

3. The device according to claim 1, wherein the light collecting unit comprises one or more lenses for projecting and/or imaging the light reflected from said surface of the product on a light sensor.

4. The device according to claim 1, wherein the illuminating beam source is configured for projecting the light beam along a central axis of the jet of pressurized fluid from the nozzle.

5. The device according to claim 1, wherein the nozzle comprises one or more jet vectoring members, wherein the one or more jet vectoring members are arranged inside said nozzle.

6. The device according to claim 5, wherein the one or more jet vectoring members comprises a series a separation walls which extend in a direction substantially parallel to a central axis of the jet, or
    wherein the one or more jet vectoring members comprises a series of substantially parallel tubes which extend in a direction substantially parallel to a central axis of the jet.

7. A device for performing an analysis of a dough product, said device comprising:
    a distance sensor configured for contactless measuring a distance between the device and a surface of the dough product, and
    a nozzle configured for directing a jet of pressurized fluid to a position on the surface of said dough product, wherein the jet of pressurized fluid is configured for providing a deformation of the surface of said dough product,
    wherein the distance sensor is arranged for measuring the distance between the device and the position on the surface of the dough product where the jet of pressurized fluid is and/or has been directed to for monitoring a development and/or a decrease or removal of the deformation of the surface of said dough product, wherein the device comprises a temperature sensor, wherein the temperature sensor is configured for measuring a temperature of said dough product, wherein the temperature sensor comprises a contactless temperature sensor.

8. The device according to claim 7, wherein the device comprises a supply tube for supplying said fluid, wherein said supply tube comprises a second branch for providing at least part of said fluid in the supply tube to the temperature sensor, or wherein the device comprises a first supply tube for supplying said fluid, and a further supply tube for supplying a cleaning fluid to the temperature sensor.

9. The device according to claim 1, wherein the fluid comprises a gas.

10. The device according to claim 1, wherein the device comprises a nozzle for producing a jet of pressurized fluid with an elongated cross-section, wherein said elongated cross-section comprises a longitudinal direction.

11. The device according to claim 1, wherein the device comprises a series of nozzles each one for producing a jet of pressurized fluid, wherein said series of nozzles are arranged in a substantially linear row.

12. The device according to claim 1, wherein the device comprises a line shaped illuminating beam, wherein said line shaped illuminating beam is configured for providing a line of light on the product surface, wherein the distance sensor comprises a camera and an image analysis processor which is configured to analyze a deformation of said line of light due to the development and/or a removal of the deformation of the surface of said dough product by the jet of compressed fluid.

13. An assembly for processing of dough products, wherein the assembly comprising:

a processing and/or conveying apparatus for said dough products, and a device for performing an analysis of a dough product according to claim 1, wherein the device is arranged for directing the jet of pressurized fluid to a position on a surface of one of said dough products in the assembly.

14. A method for a contactless analysis of a dough product, wherein said method comprising the steps of:

providing a device comprising a distance sensor;

contactlessly measuring a distance between the device and a surface of the dough product using the distance sensor and directing a jet of pressurized fluid to apply a force to a position on the surface of the dough product, wherein the jet of pressurized fluid is configured to provide a deformation of the surface of said dough product, and wherein the distance sensor measures the distance between the device and the surface of the dough product at the position of the deformation of the surface of the dough product due to the applied force and/or due to the removal of said applied force.

15. The method according to claim 14, wherein the distance sensor measures the distance between the device and the position of the surface where the jet of pressurized fluid is directed to, as a function of time.

16. The method according to claim 14, wherein the distance sensor acquires a series of measurements when said jet of pressurized fluid applies a force to the position on the surface of the product.

17. The method according to claim 14, wherein the product is covered by a liquid coating, wherein the jet of pressurized fluid pushes away said liquid coating at the position on the surface of the product, wherein the distance sensor measures the distance between the device and the position of the surface where the jet of pressurized fluid is directed to, preferably before and during the jet of pressurized fluid pushes away said liquid coating.

18. The method according to claim 14, wherein the method comprises using a device for performing the contactless analysis of the dough product, wherein said device comprises a distance sensor configured for contactless measuring a distance between the device and a surface of the dough product, and a nozzle configured for directing a jet of pressurized fluid to a position on the surface of said dough product, wherein the jet of pressurized fluid is configured for providing a deformation of the surface of said dough product, wherein the distance sensor is arranged for measuring the distance between the device and the position on the surface of the dough product where the jet of pressurized fluid is and/or has been directed to for monitoring a development and/or a decrease or removal of the deformation of the surface of said dough product, wherein the distance sensor includes an illuminating beam source for projecting a light beam at least to the position on the surface of the dough product, and a light collecting unit for receiving light reflected from said surface of the dough product, wherein the light collecting unit is configured for providing a measure of the distance between the light collecting unit and the position on the surface of the dough product where the light beam impinges on said surface, and wherein the device further includes a supply tube for supplying said fluid, wherein said supply tube comprises a first branch for providing at least part of said fluid in the supply tube to the light collecting unit, or a first supply tube for supplying said fluid, and a second supply tube for supplying a cleaning fluid to the light collecting unit.

19. The method according to claim 14, wherein the method is a method for the contactless analysis of the dough product before the dough product is finally baked in an oven.

20. The method according to claim 14, wherein the method further comprises the steps of:

monitoring the development and/or removal of the deformation by means of the distance sensor; and determining from said development and/or removal of the deformation of the surface by the jet of pressurized fluid, a measure of a viscosity and/or elasticity of the dough product.

21. The device according to claim 1, wherein the device further includes a supply tube for supplying said fluid, wherein said supply tube comprises a first branch for providing at least part of said fluid in the supply tube to the light collecting unit.

22. The device according to claim 1, wherein the device further includes a first supply tube for supplying said fluid, and a second supply tube for supplying a cleaning fluid to the light collecting unit.

\* \* \* \* \*